United States Patent [19]

Cugola et al.

[11] Patent Number: 5,686,461
[45] Date of Patent: Nov. 11, 1997

[54] INDOLE DERIVATIVES

[75] Inventors: Alfredo Cugola; Giovanni Gaviraghi; Fabrizio Micheli, all of Verona, Italy

[73] Assignee: Glaxo Wellcome S.p.A., Verona, Italy

[21] Appl. No.: 507,384

[22] PCT Filed: Mar. 3, 1994

[86] PCT No.: PCT/EP94/00614

§ 371 Date: Sep. 18, 1995

§ 102(e) Date: Sep. 18, 1995

[87] PCT Pub. No.: WO94/20465

PCT Pub. Date: Sep. 15, 1994

[30] Foreign Application Priority Data

Mar. 5, 1993 [GB] United Kingdom ............... 9304500

[51] Int. Cl.⁶ .................. C07D 453/02; A61K 31/44
[52] U.S. Cl. .................. 514/278; 514/413; 514/419; 514/278; 514/305; 514/409; 546/133; 548/491; 548/455; 548/407; 548/408
[58] Field of Search .................. 514/413, 419, 514/278, 305, 409; 546/133; 548/491, 455, 407, 408

[56] References Cited

U.S. PATENT DOCUMENTS

| | | | |
|---|---|---|---|
| 4,960,786 | 10/1990 | Salituro et al. | 514/419 |
| 5,218,123 | 6/1993 | Horwell et al. | 546/273 |
| 5,284,862 | 2/1994 | Bigge et al. | 514/419 |
| 5,519,048 | 5/1996 | Salituro et al. | 514/419 |

FOREIGN PATENT DOCUMENTS

| | | |
|---|---|---|
| A-0 568 136 | 11/1993 | European Pat. Off. |
| 92/04045 | 3/1992 | WIPO |
| WO-A-92 16205 | 10/1992 | WIPO |
| 94/27964 | 12/1994 | WIPO |

Primary Examiner—Joseph McKane
Assistant Examiner—Richard S. Myers, Jr.
Attorney, Agent, or Firm—Bacon & Thomas

[57] ABSTRACT

The invention relates to compounds of formula (I).

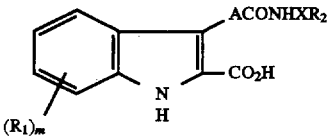

or a salt, or metabolically labile ester thereof wherein $R_1$ represents a group selected from halogen, alkyl, alkoxy, amino, alkylamino, dialkylamino, hydroxy, trifluoromethyl, trifluoromethoxy, nitro, cyano, $SO_2R_3$ or $COR_3$ wherein $R_3$ represents hydroxy, methoxy, or amino; m is zero or an integer 1 or 2;

A represents an ethynyl group or an optionally substituted ethenyl group;

X represents a bond or a $C_{1-4}$ alkylene chain;

$R_2$ represents a bridged cycloalkyl or bridged heterocyclic group; which are antagonists of excitatory amino acids, to processes for their preparation and to their use in medicine.

10 Claims, No Drawings

INDOLE DERIVATIVES

This application is a 371 filing of PCT/EP94/00614, filed Mar. 3, 1994. This invention relates to novel indole derivatives to processes for their preparation, to pharmaceutical compositions containing them and to their use in medicine. In particular it relates to indole derivatives which are potent and specific antagonists of excitatory amino acids.

U.S. Pat. No. 4,960,786 discloses that certain known 2-carboxylic indole derivatives are antagonists of excitatory amino acids. EP-A 0396124 also teaches certain 2-carboxylic indole derivatives as being therapeutically effective in the treatment of CNS disorders resulting from neurotoxic damage or neuredegenerative diseases. Further 3-substituted-2-carboxyindole derivatives which are useful in the treatment of neurodegenerative diseases including cerebrovasular disorders are disclosed in WO92/16205.

We have now found a novel group of 3-substituted-2-carboxyindole derivatives that have a specific antagonist activity at the strychnine insensitive glycine binding site located on the NMDA receptor complex.

Accordingly the present invention provides a compound of formula (I).

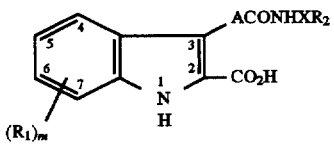

or a salt, or metabolically labile ester thereof wherein $R_1$ represents a group selected from halogen, alkyl, alkoxy, amino, alkylamino, dialkylamino, hydroxy, trifluoromethyl, trifluoromethoxy, nitro, cyano, $SO_2R_3$ or $COR_3$ wherein $R_3$ represents hydroxy, methoxy, or amino; m is zero or an integer 1 or 2;

A represents an ethynyl group or an optionally substituted ethenyl group;

X represents a bond or a $C_{1-4}$alkylene chain;

$R_2$ represents a bridged cycloalkyl or bridged heterocyclic group.

The compounds represented by formula (I) can exist in more than one isomeric form and all possible isomers are included in formula (I). Thus when the group A in compounds of formula (I) is an optionally substituted ethenyl group there can exist cis (Z) and trans (E) isomers and the invention includes all such isomers and mixtures thereof.

For use in medicine the salts of the compounds of formula (I) will be physiologically acceptable thereof. Other salts however may be useful in the preparation of the compounds of formula (I) or physiologically acceptable salts thereof. Therefore unless otherwise stated references to salts includes both physiologically acceptable salts and non-physiologically acceptable salts of compounds of formula (I).

Suitable physiologically acceptable salts of compounds of the invention include base addition salts and where appropriate acid addition salts. Suitable physiologically acceptable base addition salts of compounds of formula (I) include alkali metal or alkaline metal salts such as sodium, potassium, calcium, and magnesium, and ammonium salts formed with amino acids (e.g. lysine and arginine) and organic bases (e.g. procaine, phenylbenzylamine, ethanolamine diethanolamine and N-methyl glucosamine).

It will be appreciated that the compound of formula (I) may be produced in vivo by metabolism of a suitable prodrug. Such prodrugs may be for example physiologically acceptable metabolically labile esters of compounds of the general formula (I). These may be formed by esterification, for example of any of the carboxylic acid groups in the parent compound of general formula (I) with where appropriate prior protection of any other reactive groups present in the molecule followed by deprotection if required. Examples of such metabolically labile esters include $C_{1-4}$alkyl esters e.g. methyl or ethyl esters, substituted or unsubstituted aminoalkyl esters (e.g. aminoethyl, 2-(N,N-diethylamino) ethyl, or 2-(4-morpholino)ethyl esters) or acyloxyalkyl esters such as, acyloxymethyl or 1-acyloxyethyl e.g. pivaloyloxymethyl, 1-pivaloyloxyethyl, acetoxymethyl, 1-acetoxyethyl, 1-methoxy-1-methyl-ethylcarbonyloxyethyl, 1-benzoyloxyethyl, isopropoxycarbonyloxymethyl, 1-isopropoxycarbonyloxyethyl, cyclohexylcarbonyloxymethyl, 1-cyclohexylcarbonyloxyethyl ester, cyclohexyloxycarbonyloxymethyl, 1-cyclohexyloxycarbonyloxyethyl, 1-(4-tetrahydropyranyloxycarbonyloxyethyl) or 1-(4-tetrahydropyranylcarbonyloxyethyl.

The compounds of formula (I), salts thereof or metabolically labile esters thereof may form solvates (e.g. hydrates) and the invention includes all such solvates.

In compound of formula (I) the group $R_1$ may be at any of the four possible positions on the fused benzene ring and when m is 2 the two R groups may be the same or different.

The term alkyl as used herein as a group or part of a group refers to a straight or branched chain alkyl group containing from 1 to 4 carbon atom examples of such groups include methyl, ethyl, propyl, isopropyl, n-butyl, isobutyl, secondary butyl or tertiary butyl.

The term halogen refers to a fluorine, chlorine or bromine atom.

The term optionally substituted ethenyl means an ethenyl group optionally substituted by 1 or 2 alkyl groups e.g. methyl groups and includes both the cis and trans isomers. Examples of such groups include ethenyl, 1-methylethenyl, 2-methylethenyl and/or 1,2-dimethylethenyl.

The term bridged cycloalkyl refers to a bridged cycloalkyl group containing from 7 to 10 carbon atoms, which group is saturated or contains a single double bond. Examples of suitable bridged cycloalkyl groups include adamantyl such as 1-adamantyl or 2-adamantyl, noradamantyl e.g. 3-noradamantyl, bicyclo (2,2,1) heptanyl such as 2-norbornanyl e.g. 2-endo-2-norbornanyl or 2-exo-2-norbornanyl or bicyclo (2,2,1) heptenyl such as 5-norbornenyl, or bornyl e.g. endo-bornyl or isobornyl e.g. exo-isobornyl.

The term bridged heterocyclic refers to a bridged heterocyclic ring system containing from 7 to 10 ring members selected from carbon, oxygen or nitrogen and which bridged heterocyclic system is saturated or contains a single double bond. Preferably the bridged heterocyclic group contains a single heteroatom selected from oxygen or nitrogen. Examples of suitable bridged heterocyclic groups include 7-oxa-bicyclo (2,2,1) heptanyl, 7-oxa-bicyclo (2,2,1) heptenyl, 7-aza-bicyclo (2,2,1)heptanyl, 7-aza-bicyclo (2,2,1) heptenyl or 1-azabicyclo (2,2,2) octanyl such as 3-quinuclidinyl.

A preferred class of compounds of formula (I) are those wherein m is 1 or 2 and within this class those wherein $R_1$ is at the 4 and/or 6 position are particularly preferred.

The group $R_1$ is preferably a chlorine atom.

A particularly preferred class of compounds are those wherein m is 2 and $R_1$ is chlorine at the 4 and 6 postion in the indole ring.

When A is an optionally substituted ethenyl group it is preferably in the E configuration (trans isomer) and most preferably ethenyl or 1-methylethenyl.

The group A is conveniently an ethynyl, ethenyl or 1-methylethenyl group. A particularly preferred group A is unsubstituted ethenyl in the E configuration.

Compounds wherein X is a methylene group or more particularly a bond represent a further preferred class of compounds of formula (II).

A preferred class of compound of formula (I) are those wherein $R_2$ is a bridged $C_{7-10}$cycloalkyl group e.g.. 1-adamantyl, 3-noradamantyl or 2-exo-2-norbornanyl.

A further preferred class of compounds of formula (I) are those wherein $R_2$ is a bridged heterocyclic group containing a single nitrogen atom e.g. 3-quinuclidinyl.

A preferred group of compounds of formula (I) are those wherein m is 2, $R_1$ is chlorine in the 4 and 6 position of the indole ring, X is a bond, and $R_2$ is 2-exo-2-norbornanyl or more particular 1-adamantyl or 3-noradamantyl. From within this group particularly preferred compounds include those wherein A is ethenyl in the E configuration.

A particularly preferred compound is:

(E)-3[2-(1-adamantylcarbamoyl)ethenyl]4,6-dichloroindole-2-carboxylic acid and physiologically acceptable salts thereof e.g. sodium or potassium salts or metabolically labile esters thereof.

Further preferred compounds include:

(E) 3-[2-(exo-2-norbornylcarbamoyl)ethenyl]4,6-dichloroindole-2-carboxylic acid;

(E) 3-[2'-(noradamantyl-3"-aminocarbonyl) ethenyl]-4,6-dichloroindole-2-carboxylic acid and physiologically acceptable salts thereof or metabolically labile esters thereof.

The compounds of formula (I) and or physiologically acceptable salts thereof are excitatory amino add antagonists. More particularly they are potent antagonists at the strychnine insensitive glycine binding site associated with the NMDA receptor complex. As such they are potent antagonists of the NMDA receptor complex. Moreover the compounds of the invention exhibit an advantageous profile of activity including good bioavailibility. These compounds are therefore useful in the treatment or prevention of neurotoxic damage or neurodegenerative diseases. Thus the compounds are useful for the treatment of neurotoxic injury which follows cerebral stroke, thromboembolic stroke, hemorrhagic stroke, cerebral ischemia, cerebral vasospam, hypoglycemia, anaesia, hypoxia, anoxia, perinatal asphyxia cardiac arrest. The compounds are useful in the treatment of chronic neurodegenerative diseases such as; Huntingdon's disease, Alzheimer's senile dementia, amyotrophic lateral sclerosis, Glutaric Acidaemia type, multi-infarct dementia, status epilecticus, contusive injuries (e.g. spinal cord injury), viral infection induced neurodengeration, (e.g. AIDS, encephalopaties), Down syndrome, epilepsy, schizophrenia, depression, anxiety, pain, neurogenic bladder, irritative bladder disturbances, drug dependency, including withdrawal symptoms from alcohol, cocaine, opiates, nicotine, benzodiazepine, and emesis.

The potent and selective action of the compound of the invention at the strychnine- insensitive glycine binding site present on the NMDA receptor complex may be readily determined using conventional test procedures. Thus the ability to bind at the strychnine insensitive glycine binding site was determined using the procedure of Kishimoto H et al. J Neurochem 1981, 37 1015–1024. The selectivity of the action of compounds of the invention for the strychnine insensitive glycine site was confirmed in studies at other ionotropic known excitatory amino acid receptors. Thus compound of the invention were found to show little or no affinity for the kainic acid (kainate) receptor, a-amino-3-hydroxy-5-methyl-4-isoxazole-proprionic acid (AMPA) receptor or at the NMDA binding site.

Compounds of the invention have also been found to inhibit NMDA induced convulsions in mice using the procedure Chiamulera C et al. Psychopharmacology (1990) 102, 551–552.

The neuroprotective activity of compounds of the invention has also been demonstrated in the middle cerebral artery occulsion preparation in mice, using the procedure described by Chiamulera C et al. European Journal of Pharmacology 216 (1992) 335–336.

The invention therefore provides for the use of a compound of formula (I) and or physiologically acceptable salt or metabolically labile ester thereof for use in therapy and in particular use as medicine for antagonising the effects of excitatory amino acids upon the NMDA receptor complex.

The invention also provides for the use of a compound of formula (I) and/or a physiologically acceptable salt or metabolically labile ester thereof for the manufacture of a medicament for antagonising the effects of excitatory amino acids upon the NMDA receptor complex.

According to a further aspect the invention also provides for a method for antagonising the effects of excitatory amino acids upon the NMDA receptor complex, comprising administering to a patient in need thereof an antagonistic amount of a compound of formula (I) and/or a physiologically acceptable salt or metabolically labile ester thereof.

It will be appreciated by those skilled in the art that reference herein to treatment extends to prophylaxis as well as the treatment of established diseases or symptoms.

It will further be appreciated that the amount of a compound of the invention required for use in treatment will vary with the nature of the condition being treated the route of administration and the age and the condition of the patient and will be ultimately at the discretion of the attendant physician. In general however doses employed for adult human treatment will typically be in the range of 2 to 800 mg per day, dependent upon the route of administration.

Thus for parenteral administration a daily dose will typically be in the range 20–100 mg preferably 60–80 mg per day. For oral administration a daily dose will typically be within the range 200–800 mg e.g. 400–600 mg per day.

The desired dose may conveniently be presented in a single dose or as divided doses administered at appropriate intervals, for example as two, three, four or more sub-doses per day.

While it is possible that, for use in therapy, a compound of the invention may be administered as the raw chemical it is preferable to present the active ingredient as a pharmaceutical formulation.

The invention thus further provides a pharmaceutical formulation comprising a compound of formula (I) or a pharmaceutically acceptable salt or metabilcially labile ester thereof together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof.

The compositions of the invention include those in a form especially formulated for oral, buccal, parenteral, inhalation or insufflation, implant, or rectal administration. Parenteral administration is preferred.

Tablets and capsules for oral administration may contain conventional excipients such as binding agents, for example, syrup, accacia, gelatin, sorbitol, tragacanth, mucilage of starch or polyvinylpyrrolidone; fillers, for example, lactose, sugar, microcrystalline cellulose, maize-starch, calcium phosphate or sorbitol; lubricants, for example, magnesium stearate, stearic acid, talc, polyethylene glycol or silica; disintegrants, for example, potato starch or sodium starch glycollate, or wetting agents such as sodium lauryl sulphate. The tablets may be coated according to methods well known in the art. Oral liquid preparations may be in the form of, for example, aqueous or oily suspensions, solutions emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; solubilizers such as surfactants for example polysorbates or other agents such as cyclodextrins; and preservatives, for example, methyl or propyl p- hydroxybenzoates or ascorbic acid. The compositions may also be formulated as suppositories, e.g. containing conventional suppository bases such as cocoa butter or other glycerides.

For buccal administration the composition may take the form of tablets or lozenges formulated in conventional manner.

The composition according to the invention may be formulated for parenteral administration by injection or continuous infusion. Formulations for injection may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

For administration by inhalation the compounds according to the invention are conveniently delivered in the form of an aerosol spray presentation from pressurised packs, with the use of a suitable propellent, such as dichlorodifluoromethane, tirchlorofluoromethane, dichloro-tetrafluoroethane, carbon dioxide or other suitable propellent, such as dichlorodifluoromethane, trichlorofluoromethane, dichloro-tetrafluoroethane, carbon dioxide or other suitable gas, or from a nebuliser. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable carrier such as lactose or starch. The powder composition may be presented in unit dosage form in for example capsules or cartridges of e.g. gelatin, or blister packs from which the powder may be administered with the aid of an inhaler or insufflator.

The composition according to the invention may also be formulated as a depot preparation. Such long acting formulations may be administered by implantation (for example subcutaneously or intramuscularly) or by intramuscular injection. Thus for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

The compositions according to the invention may contain between 0.1–99% of the active ingredient, conveniently from 30–95% for tablets and capsules and 3–50% for liquid preparations.

Compounds of general formula (I) and salts thereof may be prepared by the general methods outlined hereinafter. In the following description, the groups $R_1$, $R_2$ and X are as defined for the compounds of formula (I) unless otherwise stated.

Compounds of formula (I) wherein the groups $R_1$, $R_2$, X, and m have the meanings defined above and A is an optionally substituted ethenyl group may be prepared by reaction of an activated derivative of the carboxyclic acid (II)

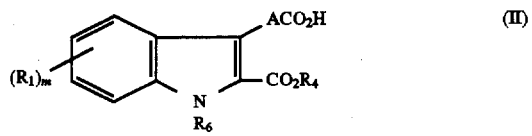

wherein $R_1$, m, and A have the meanings defined above, $R_4$ is a carboxyl protecting group, and $R_6$ is a hydrogen atom or a nitrogen protecting group, with the amine

$$H_2NXR_2 \quad \text{(III)}$$

wherein X and $R_2$ have the meanings defined above, followed by subsequent removal of the carboxyl protecting group $R_4$ and if necessary the nitrogen protecting group $R_6$.

Suitable activated derivatives of the carboxyl group include the corresponding acid halide, mixed anhydride, activated ester or the derivative formed between the carboxylic acid group and a coupling agent such as that used in peptide chemistry, for example carbonyldimidazole or a dimidide such as dicyclohexylcarbodimide.

The reaction is preferably carried out in an aprotic solvent such as a hydrocarbon, halohydrocarbon, such as dichloromethane or an ether such as tetrahydrofuran.

Suitable carboxyl protecting groups $R_4$ for use in these reactions include allyl, alkyl, trichloroalkyl, trialkylsilylalkyl or arylmethyl groups such as benzyl, nitrobenzyl or trityl.

Suitable nitrogen protecting groups include alkoxycarbonyl e.g. t-butoxycarbonyl, 2-trimethylsilylethoxymethyl or arylsulphonyl e.g. phenylsulphonyl.

The activated derivatives of the carboxylic acid (II) may be prepared by conventional means.

A particularly suitable activated derivative for use in this reaction is the ester derived from pyridine-2-thiol. These esters may conveniently be prepared by treating the carboxylic acid (II) with 2,2'-dithiopyridine and triphenylphosphine in a suitable solvent such as tetrahydrofuran.

Compounds of formula (I) wherein A is an optionally substituted ethenyl group may also be prepared from compound (IV) in which $R_1$, and m halve the means given above, $R_4$ is a carboxyl protecting group, $R_5$ is a hydrogen atom or a $C_{1-4}$alkyl group and $R_6$ is hydrogen or a nitrogen protecting group.

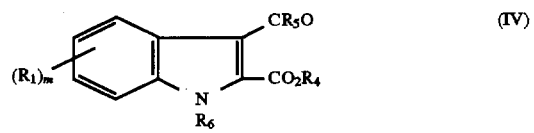

by reaction with an appropriate phosphorus ylide capable of converting the group $CR_5O$ into the group $ACONHXR_2$ wherein X and $R_2$ have the meanings defined above for formula (I) followed where necessary or desired by removal of the nitrogen protecting and or the carboxyl protecting group.

Suitable carboxyl protecting groups include allyl, alkyl, trichloroalkyl, trialkylsilylalkyl or arymethyl groups such as benzyl, nitrobenzyl or trityl.

Suitable nitrogen protecting groups include alkoxycarbonyl e.g. t-butoxycarbonyl, 2-trimethylsilylethoxymethyl or arylsulphonyl e.g. phenylsulphonyl.

In one embodiment of this process the reaction may be carried using a phosphorus ylide of formula (V)

$(R_7)_3P=CHCONHXR_2$ (V)

wherein $R_7$ is an alkyl or phenyl group, and X and $R_2$ have the meanings defined above.

The reaction is carried out in aprotic solvent such as acetonitrile or an ether such as 1,4-dioxane or an aromatic hydrocarbon e.g. toluene or an alkanol e.g. isopropanol and preferably with heating e.g. 40°–120°.

In a further embodiment of the process the reaction is carried out using a phosphorus ylide of formula (VI)

$(R_8O)_2OPCH(R_9)CONHXR_2$ (VI)

wherein $R_9$ represents hydrogen or $C_{1-4}$alkyl;

$R_8$ represents $C_{1-4}$alkyl and X and $R_2$ have the meanings defined above.

The reaction is carried out in an aprotic solvent such as tetrahydrofuran and optionally with heating.

Compounds of formula (I) wherein A is an ethynyl group may be prepared by reaction of the compound (VII)

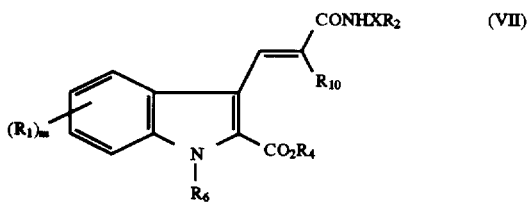

wherein $R_1$, $R_2$ and m have the meanings defined in formula (I), $R_4$ has the meaning defined in formula (IV), $R_6$ is a nitrogen protecing group and $R_{10}$ represents an halogen group such as chlorine, with a strong base such as lithium bis(trimethylsilyl)amide, followed by the removal of the protecting groups $R_6$ and $R_4$.

The reaction is preferably carried out in an aprotic solvent such as an ether e.g. tetrahydrofuran and at a temperature within the range −20° to +20° C.

The protecting groups $R_6$ and $R_4$ may be removed by conventional procedures.

Examples of suitable N-protecting groups $R_6$ include alkoxycarbonyl e.g. t-butyloxycarbonyl, or arylsulphonyl e.g. phenylsulphonyl.

Compounds of formula (I) wherein A is an unsubstituted ethenyl group with the cis configuration may be prepared from the corresponding compound of formula (I) wherein A is ethynyl or a protected derivative thereof by reduction using hydrogen and palladium on a calcium carbonate/lead oxide support as catalyst, followed where necessary by removal of any protecting group.

In any of the above reactions the carboxyl protecting group $R_4$ may be removed by conventional procedures known for removing such groups. Thus compounds when $R_4$ is an alkyl group, this may be removed by hydrolysis using an alkali metal hydroxide e.g. lithium hydroxide or sodium hydroxide in a solvent such as an alkanol e.g. ethanol or isopropanol, followed where desired or necessary by that addition of a suitable acid e.g. hydrochloric acid to give the corresponding free carboxylic acid.

In any of the above reactions the nitrogen protecting group may be removed by conventional procedures known for removing such groups, for example by acid or base hydrolysis. Thus when $R_6$ is alkoxycarbonyl e.g. t-butoxycarbonyl or phenylsulphonyl it may be removed by alkaline hydrolysis using for example lithium hydroxide or sodium hydroxide in a suitable solvent such as tetrahydrofuran or an alkanol e.g. isopropanol.

Physiologically acceptable salts of compounds of formula (I) may be prepared by treating the corresponding acid with an appropriate base in a suitable solvent. For example alkali and alkaline metal salts may be prepared from an alkali or alkaline metal hydroxide, or the corresponding carbonate or bicarbonate salts thereof. Alternatively alkali or alkaline metal salts may be prepared by direct hydrolysis of carboxyl protected derivative of compound of formula (I) with the appropriate alkali or alkaline metal hydroxide.

Metabolically labile esters of compounds of formula (I) may be prepared by esterification of the carboxylic acid group or a salt thereof or by trans esterfication using conventional procedures. Thus for example acyloxyalkyl esters may be prepared by reacting the free carboxylic acid or a salt thereof with the appropriate acyloxylalkyl halide in a suitable solvent such as dimethylformamide. For the esterification of the free carboxyl group this reaction is preferably carried out in the presence of a quaternary ammonium halide such as tetrabutylammonium chloride or benzyltriethylammonium chloride.

Aminoalkyl esters may be prepared by transesterfication of a corresponding alkyl ester e.g. methyl or ethyl ester by reaction with the corresponding aminoalkanol at an elevated temperature e.g. 50°–150°.

Compounds of formula (II) are either known compounds or may be prepared by analogous methods to those described for known compounds.

Thus compounds of formula (II) wherein A is an optionally substituted ethenyl group may be prepared from compound of formula (IV) and a phosphorus ylide $(R_7)_3P=CH$ $CO_2Bu^t$ or a phosphonate $(R_8O)_2OP-CH$ $(R_9)CO_2Bu^t$ using similar reaction conditions for those described above for the reaction of (IV) with the compounds of formula (V) or (VI) followed by removal of the t-butyl protecting group.

Compounds of formula (VII) may be prepared from a compound of formula (IV) and a phosphonate $(R_8O)_2OPCH$ $(R_{10})CONHXR_2$ using similar reaction conditions for those described above for the reaction of (IV) with the phosphonate (VI).

Compounds of formula (IV) wherein $R_4$ is a carboxyl protecting group, and $R_5$ is hydrogen may be prepared by treating the corresponding indole (IX).

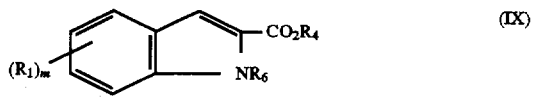

wherein $R_1$, $R_6$ and m are as defined above with N-methylformanilide and phosphorous oxychloride in a solvent such as 1,2-dichloroethane.

Compounds of formula (IV) wherein $R_4$ is a carboxyl protecting group, and $R_5$ is alkyl may be prepared by treating the indole (IX) with the amide $(CH_3)_2NCOR_5$ and phosphorous oxychloride in a suitable solvent.

The indoles of formula (IX) are either known compounds or may be prepared by analogous methods to these described for the known compounds.

The compounds of formula (V) or (VI) are either known or may be prepared using methods described for analogous compounds In order that the invention may be more fully understood the following examples are given by way of illustration only.

In the Intermediates and Examples unless otherwise stated:

Melting points (m.p.) were determined on a Gallenkamp m.p. apparatus and are uncorrected. All temperature refers to °C. Infrared spectra were mesured on a FT-IR instrument. Proton Magnetic Resonance ($^1$H-NMR) spectra were recorded at 300 MHz, chemical shifts are reported in ppm downfield (d) from Me$_4$Si, used as internal standard, and are assigned as singlets (s), doublets (d), doublets of doublets (dd), triplets (t), quartets (q) or multiplets (m). Colum chromathography was carrier out over silica gel (Merck AG Darmstaadt, Germany). The following abbrevietions are used in text: EA=ethyl acetate, CH=cyclohexane, DCM= dichloromethane, DMF=N,N-dimethylformamide, THF= tetrahydrofuran, MeOH=methanol, AcOH=glacial acetic acid. Tlc refers to thin layer chromatography on silica plates. Solution were dried over anhydrous sodium sulphate.

Intermediate 1

(E) Ethyl 3-[2-(tertbutoxycarbonyl)ethenyl]-4,6-dichloroindole-2-carboxylate

A solution of tertbutoxycarbonylmethyltriphenylphosphorane (5.33 g) and ethyl 3-formyl-4,6-dichloroindole-2-carboxylate (3 g) in dioxanlacetonitrile (1;1; 60 ml) was stirred at 60° for 7 hours. The solvent was evaported under reduced pressure and the residual oil was purified by chromatography, eluting with cyclohexane and ethyl acetate 7/3, to obtain the title compound (2,73 g) tlc EA/CH: 3/7; Rf=0.35.

$^1$H-NMR(DMSO) 12.6(s), 8.28(d), 7.51(d), 7.32(d), 6.44 (d), 4.37(q), 1.35(t).

Intermediate 2

(E) Ethyl 3-[2-carboxyethenyl]-4,6-dichloroindole-2-carboxylate

Intermediate 1 (0.5 g) was dissolved in 100% formic acid (60 ml) and the suspension was left at 23° for 2 hours. The solvent was evaporated under reduced pressure to give the title compound as a white solid (0.408 g; tlc EA/CH: 45/55; Rf=0.18).

$^1$H-NMR(DMSO) 12.6(s), 8.28(d), 7.51(d), 7.32(d), 6.44 (d), 4.37(q), 1.35(t).

Intermediate 3

(E) Ethyl 3-[2-(2-thiopyridylcarbonyl)ethyl]-4,6-dichloroindole-2-carboxylate

To a solution of Intermediate 2 (0.2 g) in tetrahydrofuran (15 ml), 2,2'-dipyridyldisulfide (0.162 g) and triphenylphosphine were added. The resulting solution was stirred at room temperature for 3 hours. The solvent was evaporated under reduced pressure to give an oil. The residue was purified by flash chromatography (CH/EA:6/4) to give the title compound (0.95 g; tlc CH/EA:6/4 Rf=0.35).

$^1$H-NMR(DMSO) 9.32(s), 8.65(m), 8.53(d), 7.80–7.76 (m), 7.35(d), 7.31(m), 7.24(d), 7.00(d), 4.47(q), 1.46(t).

Intermediate 4

Ethyl 1-Phenylsulfonyl-4,6-dichloro-3-formyl-indole-2-carboxylate

A solution of ethyl 3-formyl-4,6-dichloroindole-2-carboxylate (5.0 g) in dry DMF (30 ml) was added to a suspension of sodium hydride (0.629 g; 80% suspension in mineral oil) in dry DMF (10 ml) under nitrogen at 0°. The reaction was stirred at this temperature for 45 min then phenylsulfonyl chloride (2.5 ml) was added giving a yellow precipitate. The reaction was allowed to warm slowly to room temperature, stirred for a further 14 h then poured into water (250 ml). The solid was filtered, washed with water and then with ethyl acetate to give the title compound (4.493 g,) as a white solid, m.p. 225.8°–226.3°.

Rf=0.44 (20% EA/CH).

IR (Nujol) Vmax (cm–1) 1730 and 1682 (C=O), and 1377 (SO$_2$).

Intermediate 5

Tert-butyl dichloro(diethoxyphosphoryl)acetate

A solution of sodium hypochlorite (400 ml) was adjusted to pH=7.1 by the addition of a solution of hydrochloric acid (1N) and cooled to 8° in an ice bath. Tert-butyl (diethoxyphosphoryl)acetate (9.986 g; 95% pure) was then added with stirring and the reaction was warmed. After 2 h the turbid solution was at 20°, water (200 ml) was added and the mixture was extracted with cyclohexane (4×200 ml). The organic extracts were combined, dried and evaporated under reduced pressure to give the title compound as a colourless oil (12 g).

Rf=0.45 (50% EA/CH) (colours white with alkaline potassium permanganate spray reagent).

IR (CDCl$_3$) Vmax (cm–1) 1753 and 1747 (C=O).

Intermediate 6

Tert-butyl chloro(diethoxyphosphoryl)acetate

A solution of intermediate 5 (7.388 g) in ethanol (56.5 ml; 95%) and water (180 ml) was cooled to 0° with stirring. A solution of sodium sulphite (5.8 g) in water (20 ml) was added dropwise keeping the temperature below 15°, the cooling bath was then removed and the reaction was stirred at room temperature for 1.5 h. The reaction mixture was extracted with dichloromethane (5×100 ml), the combined organic extracts dried and evaporated under reduced pressure to give the title compound (6.404 g) as a colourless oil.

Rf=0.43 (50% EA/CH) (colours mustard with alkaline potassium permanganate spray reagent).

IR (Film) Vmax (cm$^{-1}$) 1749 (C=O), 1288 and 1267 (P=O).

Intermediate 7

Ethyl 1-phenylsulfonyl-3-[(2'-tert-butoxycarbonyl-2'-chloro)ethenyl]-4,6-dichloroindole-2-carboxylate Lithium bis(trimethylsilyl)amide (3.5 ml; 1M in THF) was added dropwise to a solution of intermediate 6 (1.009 g) in dry THF (15 ml) under nitrogen at 0°. The reaction was stirred for 45 min at this temperature then a suspension of intermediate 4 (1.5 g) in dry THF (30 ml) was added. Stirring for a further 3 h at 0° resulted in the gradual formation of a solution to which was added saturated ammonium chloride solution (10 ml). The mixture was extracted with dichloromethane (3×50 ml), the combined extracts washed with brine (1×30 ml), dried and evaporated under reduced pressure. The resulting residue was adsorbed onto silica and purified by flash chromatography using 15% EA/CH as eluant to give the title compound (1.339 g) as a white solid and as mixture of E and Z isomers.

Rf=0.48 (20% EA/CH).

$^1$H-NMR (CDCl$_3$) Major isomer: 8.04 (2H, dd), 8.01 (1H, d), 8.00 (1H, s), 7.65 (1H, tt), 7.55 (2H, td), 7.28 (1H, d), 4.41 (2H, q), 1.56 (9H, s), and 1.37 (3H, t). Minor isomer: 8.09 (2H, dd), 8.0 (1H, d), 7.55 (2H, td), 4.41 (2H, q), and 1.37 (3H, t).

Intermediate 8

Ethyl E- and Z- 1-Phenylsulfonyl-3[(2'-carboxy-2'-chloro)ethenyl]-4,6-dichloroindole-2-carboxylate A suspension of intermediate 7 (3.025 g) in formic acid (150 ml) was stirred for 2 h at room temperature then left standing for 15 h. The resulting white suspension was evaporated to dryness and the trituration with diethyl ether gave the title compound (1.198 g) as a white solid containing starting material (4%).

¹H-NMR (DMSO) 8.10–8.00 (2H, m), 8.06 (1H, s), 7.52 (1H, s), 8.05 (1H, d) 7.95 (1H, d), 7.8–7.6 (3H, m), 7.65 (1H, d), 7.59 (1H, d), 4.32 (2H, q), 4.30 (2H, q), 1.25 (3H, t), 1.23 (3H, t), 13.08 (1H, DS).

Intermediate 9

Ethyl E- and Z-3-(2'-(1-Adamantylcarbamoyl)-2'-chloroethenyl)-1-phenylesulfonyl-4,6-dichloroindole-2-carboxylate Dipyridyl disulfide (503 mg) and triphenyl phosphine (598 mg) were added to a solution of intermediate 8 (750 mg) in dry THF (17 ml) and the resulting yellow solution was stirred at room temperature for 2.5 h. 1-Adamantanamine (270 mg) was added and the reaction was refluxed for 2 h, evaporated to dryness and the resulting residue was purified by flash chromatography using 10% EA/CH as eluant to give the title compound (621 mg,) as a white foam.

IR (Nujol) $v_{max}$(cm⁻¹) 3422 (NH), 1734 (ester C=O), 1640 (amide C=O).

¹H-NMR (DMSO) E and Z isomers: 8.09 (m), 8.07 (m), 8.03(d), 7.97 (d), 7.86 (s), 7.81 (t), 7.69 (m), 7.64 (d), 7.61 (d), 7.25 (s), 7.15 (s), 6.94 (s), 4.34 (m), 2.05 (m), 1.88 (m), 1.70–1.40 (m), and 1.25 (m).

Intermediate 10

Ethyl 3-(2'-(1-Adamantylcarbamoyl)-ethynyl)-1-phenylsulfonyl-4,6-dichloroindole-2-carboxylate A solution of intermediate 9 (444 mg) in dry THF (8 ml) was cooled to −60° C. under nitrogen and lithium bis-(trimethylsilyl)amide (1.85 ml; 1M) was added dropwise to give a yellow solution. The reaction was stirred for 1.5 h at between −50° C. and −60° C. then was warmed over 1 h to −5° C. Saturated ammonium chloride solution (5 ml) was added and the mixture was extracted with ethyl acetate (3×25 ml). The combined extracts were washed with brine, dried, filtered and the solvent removed in vacuo. The resulting residue was purified by flash chromatography using 8% followed by 25% EA/CH to give the title compound (314 mg,) as a pink solid.

IR (Nujol) $v_{max}$(cm⁻¹) 3389 (NH), 2206 (triple bond), 1732 (C=O ester), and 1661 (C=O amide).

NMR (CDCl₃) 8.06 (d), 7.96 (d), 7.66 (t), 7.55 (t), 7.31 (d), 5.48 (s), 4.54 (q), 2.09 (m), 2.03–1.68 (m), and 1.47 (t).

EXAMPLE 1

(E) Ethyl 3-[2-(1-adamantylcarbamoyl)ethenyl]4,6-dichloroindole-2-carboxylate

To a solution of intermediate 3 in dry THF (13 ml), 1-adamantanamine (180 mg) was added in two portions over 4 hours. The solvent was evaporated under pressure and the residue was triturated with dichloromethane. The resulting precipitate was filtered to give a solid containing aliphatic impurities which were removed by stirring overnight in n-hexane. After filtration the pure title compound was obtained (180 mg) tlc (EA:CH=1:1Rf=0.54). m.p. 150–152.

IR(Nujol) Vmax (cm⁻¹) 3335 (NH), 1672 (C=O), 1675 (C=O), 1614 (C=C).

¹H-NMR(DMSO) 11.6(s), 7.98(d), 7.57(s), 7.47(d), 7.24 (d), 6.52(d), 4.34(q), 2.10–1.90(m), 1.64(m), 1.34(t).

EXAMPLE 2

(E) Ethyl-3-[2-exo-2-norbornylcarbamoyl)ethenyl]4,6-dichloroindole-2-carboxylate To a solution of intermediate 2 (0.30 g) in dry THF (19 ml), 2,2'dithiopyridine (0.306 g) and triphenylphosphine (365 mg) were added in two portions over 1.5 hours at room temperature. 2 Exo-aminonorborane (221 mg) was added in two portions over 2 hours. The solvent was evaporated under pressure and the residue was triturated with ethyl acetate. The solid was filtered and purified by trituration with hot ethyl acetate to give the pure title compound (230 mg) tlc (EA:CH-1:1 Rf −0.38. m.p. 250.

IR(Nujol) Vmax (cm⁻¹) 3330 (NH), 1676 (C=O), 1659 (C=O), 1622 (C=C).

¹H-NMR(DMSO) 11.9(s), 8.03(d), 7.97(d), 7.48(d), 6.52 (d), 4.35(q), 3.64(m), 2.30–2.10(m), 1.62(m), 1.50–1.30(m), 1.33(t), 1.20–1.00(m).

EXAMPLE 3

(E) Ethyl-3-[2-endo-2-norbornylcarbamoyl)ethenyl]4,6-dichloroindole-2-carboxylate To a solution of intermediate 2 (0.3 g), in dry THF (20 ml), 2,2'-dipyridyl disulfide (268 mg, 1.30 mmol) and triphenylphosphine (341 mg, 1.30 mmol) were added and the solution was stirred at room temperature for 1.5 hours. A preformed suspension of endo-2-aminonorborane hydrochloride (294 mg, 1.99 mmol) and triethylamine (0.270 ml) in dry THF (5 ml), stirred at room temperature for 1.5 hours was then added. After 1.5 hours the solvent was evaporated under reduced pressure and the residue dissolved in ethyl acetate and was washed with water. The organic layer, was concentrated and the resulting precipitate was filtered to give the title compound (240 mg).

tlc (EA/CH=1:1 Rf=0.38), m.p.=242°–2440.

¹H-NMR:(DMSO) 12.15(s), 8.07(d), 8.01(d), 7.48(d), 7.27(d), 6.57(d), 4.34(q), 4.03(m), 2.31(s), 2.14(s), 1.88(m), 1.6–1.2(m), 1.23(s), 1.32(t), 0.90(m).

IR(Nujol)cm⁻¹ 3312(NH), 1680(C=O), 1616(C=C).

EXAMPLE 4

(E) Ethyl-3-[2-(3-Quinuclidinearbamoyl)ethenyl]4,6-dichloroindole-2-carboxylate

To a solution of intermediate 2 (130 ml) in dry THF (8 ml) 2,2'dipyridyl disulfide (135 mg) and triphenylphosphine (113 mg) were added. The solution was stirred at room temperature for 1.5 hours, then 3-aminoquinuclidine hydrochloride (100 mg) and triethylamine (0.100 ml) were added. The solution was stirred at room temperature for 18 hours. The resulting precipitate was filtered, dissolved in water and the pH of the solution adjusted at pH=7. The mixture was extracted with ethyl acetate and the organic layer was dried and evaporated under reduced pressure to give the title compound (110 mg) as a white solid.

tlc (DCM/MeOH=95.5 Rf=0.41), m.p.=157°–159°.

¹H-NMR:(DSMO) 12.5(s), 8.2(d), 8.0(d), 7.47(d), 7.30 (d), 6.6(d), 4.34(q), 3.84(m), 2.8–1.2(m), 1.32(t).

IR (Nujol)cm⁻¹ 1718–1680(C=O), 1616–1543(C=C).

EXAMPLE 5

(E) Ethyl 3-[2'-(1"-adamantylmethylaminocarbonyl) ethenyl]-4,6-dichloroindole-2-carboxylate To a solution of intermediate 2 (0.30 g) in dry THF (20 ml), 2,2'-dipyridyl disulfide (282 mg) and triphenylphosphine (336 mg) were added. The solution was stirred at room temperature for 1.5 hours, then 1-adamantanemethylamine (0.12 ml) was added. The resulting mixture was stirred at room temperature for 14 hours, then the solvent was removed under reduced pressure, the residue was suspended in ethyl acetate and filtered to give the title compound (260 mg) as a white solid.

tlc (EA/CH=1/1 Rf=0.53), m.p.>250° C.

$^1$H-NMR:(DMSO) 12.6(bs), 8.0(d), 7.94(bt), 7.47(d), 7.27(d), 6.56(d), 4.34(q), 2.89(d), 1.91(bm), 1.6(m), 1.32(t)

IR(Nujol)cm$^{-1}$ 3306(NH), 1680(C=O), 1556(C=O)

EXAMPLE 6

(E) Ethyl 3-[2'-(noradamantyl-3"-aminocarbonyl) ethenyl]-4,6-dichloroindole-2-carboxylate To a solution of intermediate 2 (0.254 g) in dry THF (15 ml), 2,2'-dipyridyl disulfide (239 mg) and triphenylphosphine (284 mg) were added. The solution was stirred at room temperature for 1.5 hours then 3-noradamantanamine (114 mg) was added and the mixture was left at room temperature for 18 hours. The solvent was evaporated, the solid was suspended in water and extracted with ethyl acetate to obtain a crude which was purified by flash-chromatography (CH/EA=65/35). The solid was crystallized using ethanol giving the title compound (190 mg) as white solid.

tlc (CH/EA=6/4 Rf=0.360) m.p. 138°–139° C.

$^1$H-NMR:(DMSO) 12.49(bs), 8.15(bs), 8.02(d), 7.49(d), 7.29(d), 6.56(d), 4.36(q), 2.43(m), 2.22(m), 2.07(m), 1.96 (m), 1.84(dd), 1.62–1.46(m), 1.34(t)

IR(Nujol)cm$^{-1}$ 3368–3167(NH), 1718(C=O), 1652 (C=O), 1639(C=O),1610(C=C)

EXAMPLE 7

(E) Ethyl-3-[2'-(1"-R-isobornyl-2"-aminocarbonyl) ethenyl]-4,6-dichloroindole-2-carboxylate To a solution of intermediate 2 (0.30 g) in dry THF (20 ml), 2,2'-dipyridyl disulfide (282 mg) and triphenylphosphine (336 mg) were added and the solution was stirred at room temperature for 1.5 hours. A preformed suspension of R(-)-isobornylamine hydrochloride (209 mg) and triethylamine (0.15 ml) in dry THF (5 ml), stirred at room temperature for 1.5 hours was added and the reaction was stirred at room temperature for 15 hours. The solvent was removed under reduced pressure and the residue was dissolved in ethyl acetate and was washed with water. The organic layer was dried, the solvent evaporated and the residue was purified by flash-chromatography (CH/EA=6/4). The solid was crystallized using ethanol to give the title compound (230 mg) as a white solid.

tlc (CH/EA=6/4 Rf=0.35) m.p.210°–211° C.

$^1$H-NMR:(DMSO) 12.48(bs), 7.98(d), 7.47(d), 7.27(d), 6.61(d), 4.4–4.25(m), 3.86(m), 1.50(m), 1.15(m), 1.31(t), 0.91(s), 0.78(s)

IR(Nujol)cm$^{-1}$ 3400(N H), 1703(C=O), 1682(C=O), 1624(C=C)

EXAMPLE 8

(E) Ethyl-3-[2'-(1"-R-bornyl-2"-aminocarbonyl) ethenyl]-4,6-dichloroindole-2-carboxylate To a solution of intermediate 2 (0.30 g) in dry THF (20 ml), 2,2'-dipyridyl disulfide (282 mg) and triphenylphosphine (336 mg) were added. The solution was stirred at room temperature for 1.5 hours, then R(+)-bornylamine (169 mg) was added. The resulting mixture was stirred at room temperature for 14 hours, then the solvent was removed under reduced pressure and the residue was dissolved in ethyl acetate and was washed with water. The organic layer was dried, the solvent evaporated and the residue was purified by flash-chromatography (CH/EA=65/35) to give the title compound (309 mg) as a white solid.

tlc (CH/EA=1/1 Rf=0.47)

1H-NMR:(DMSO) 12.51(bs), 8.03(d), 7.96(bd), 7.49(d), 7.29(d), 6.64(d), 4.36(m), 4.24(m), 2.18(m), 1.70–1.60(m), 1.40–1.20(m), 0.92(m), 1.33(t), 0.93(s), 0.85(s), 0.74(s)

IR(Nujol)cm$^{-1}$ 3312(NH), 1682–1657(C=O), 1614 (C=C)

EXAMPLE 9

(E) Ethyl-3-[2'-(2"-adamantylaminocarbonyl) ethenyl]-4,6-dichloroindole-2-carboxylate To a solution of intermediate 2 (0.30 g) in dry THF (20 ml), 2,2'-dipyridyl disulfide (282 mg) and triphenylphosphine (336 mg) were added and the solution was stirred at room temperature for 1.5 hours. A preformed suspension of 2-adamantanamine hydrochloride (206 mg) and triethylamine (0.15 ml) in dry THF (5 ml), stirred at room temperature for 1.5 hours was added and the reaction was stirred at room temperature for 3.5 hours. The solvent was removed under reduced pressure and the residue was suspended in ethyl acetate and filtered to give the title compound (312 mg) as a white solid.

tlc (CH/EA=1/1)

EXAMPLE 10a (E)-3-(2'-(1-Adamantylcarbamoyl)ethenyl)-4,6-dichloroindole-2-carboxylic acid sodium salt Example 1 (200 mg), sodium hydroxide (69 mg) and isopropyl alcohol (8 ml) were heated at 60° C. for 4 h with stirring. Water (10 ml) was added, the isopropyl alcohol was removed under reduced pressure and the resulting precipitate was filtered and washed with water giving the title compound (190 mg) as a cream solid.

IR (Nujol) $v_{max}$ (cm$^{-1}$) 3418 and 3360 (NH), 1647 and1603 (C=O).

$^1$H-NMR (DMSO) 11.54 (bs), 8.29 (d), 7.37 (d), 7.25 (s), 7.05 (d), 6.79 (d), 1.98 (m), 1.62 (m).

EXAMPLE 10b (E)-3-(2'-exo-2-norbornylcarbamoyl)ethenyl)-4,6-dichloroindole-2-carboxylic acid sodium salt Example 2 (265 mg), sodium hydroxide (100 mg) and isopropyl alcohol (5 ml) were heated at 60° C. for 2 h with stirring. Water (8 ml) was added, the isopropyl alcohol was removed under reduced pressure and the resulting precipitate was filtered and washed with water giving the title compound (150 mg; 58) as a cream solid.

IR (Nujol) $v_{max}$ (cm$^{-1}$) 3414 and 3194 (NH), 1651 and 1607 (C=O).

$^1$H-NMR (DMSO) 12.0–11.4 (bs), 8.34 (d), 7.73 (d), 7.38 (d), 7.05 (d), 6.84 (d), 3.60 (m), 2.18 (bs), 2.08 (bs), and 1.6–1.0 (m).

EXAMPLE 11

(E) 3-[2-endo-2-norbornylcarbamoyl)ethenyl]4,6-dichloroindole-2-carboxylic acid sodium salt To a suspension of Example 3 (100 mg) in isopropyl alcohol (4 ml), sodium hydroxide (38 mg) was added. The solution was heated at 700 for 1 hour, then the solvent was evaporated under reduced pressure. The residue was suspended in water and filtered to give the title compound as a white solid (77 mg), ¹H-NMR:(DMSO) 11.69(s), 8.34(d), 7.84(d), 7.05), 6.87 (d), 4.00(m), 2.29(m), 2.11(m), 1.90–1.09(m).

IR (Nujol)cm$^{-1}$ 3420–3271 (NH), 1659(C=O), 1607 (C=C).

EXAMPLE 12

(E) 3-[2-(3-Quniuclidinecarbamoyl)ethenyl]4,6-dichloroindole-2-carboxylic acid

To a suspension of Example 4 (105 mg) in isopropyl alcohol (4 ml), sodium hydroxide (38 mg; 0.95 mmol) was added. The solution was heated at 70° for 1 hours, then the solvent was evaporated under reduced pressure. The residue was suspended in water and the pH of the solution adjusted at pH=7. The resulting precipitate was filtered to give the title compound as a white solid (87 mg).

¹H-NMR: (DMSO) 12.4(s), 11.96(s), 8.46(d), 8.28(d), 7.41(d), 7.12(d), 6.80(d), 4.14(m), 3.60–3.00(m), 2.2–1.6 (m).

IR (Nujol)cm$^{-1}$ 3366–3188(NH), 1661(C=O), 1618–1576(C=C).

EXAMPLE 13

(E) 3-[2'-(1"-adamantylmethylaminocarbonyl)ethenyl]-4,6-dichloroindole-2-carboxylic acid sodium salt To a suspension of Example 5 (261 mg) in isopropyl alcohol (20 ml), sodium hydroxide (110 mg) was added. The solution was heated at 60° C. for 4 hours, then the solvent was removed under reduced pressure. The residue was suspended in water and the precipitate was filtered to give the title compound (208 mg) as a white solid.

¹H-NMR:(DMSO) 11.7(bs), 8.37(d), 7.72(t), 7.38(d), 7.07(d), 6.94(d), 2.87(d), 1.92(m), 1.70–1.40(m)

IR(Nujol)cm$^{-1}$ 3429–3198(NH), 1653–1612(C=O)

EXAMPLE 14

(E) 3-[2'-(noradamantyl-3"-aminocarbonyl) ethenyl]-4,6-dichloroindole-2-carboxylic acid sodium salt To a suspension of Example 6 (191 mg) in isopropyl alcohol (15 ml), sodium hydroxide (68 mg) was added. The solution was heated at 60° C. for 4 hours, then the solvent was evaporated under reduced pressure. The residue was suspended in water and the precipitate was filtered to give the title compound (125 mg) as a pale yellow solid.

¹H-NMR:(DMSO) 11.50(bs), 8.30(d), 7.83(bs),7.34(d), 7.04(d), 6.87(d),2.42(t), 2.19(bs), 2.06(d), 1.94(m), 1.80(m), 1.50(m)

IR(Nujol)cm$^{-1}$ 11609 (C=O)

EXAMPLE 15

(E) 3-[2'-(1"R-isobornyl-2"-aminocarbonyl) ethenyl]-4,6-dichloroindole-2 carboxylic acid sodium salt To a suspension of Example 7 (150 mg) in isopropyl alcohol (15 ml), sodium hydroxide (52 mg) was added. The solution was heated at 60° C. for 5 hours, then the solvent was removed under reduced pressure. The residue was suspended in water, the precipitate was filtered and purified by precipitation from THF/hexane giving the title compound (125 mg) as a pale yellow solid.

¹H-NMR:(DMSO) 11.6(bs), 8.34(d), 7.36(d), 7.21(bd), 7.05(d), 6.89(d), 1.8–1.6(m), 1.48(m), 1.2–1.06(m), 0.91 (s), 0.76(s,s)

IR(Nujol)cm$^{-1}$ 3192(NH), 1609(C=C)

EXAMPLE 16

(E) 3-[2'-(1"-R-bornyl-2"-aminocarbonyl) ethenyl]-4,6-dichloroindole-2 carboxylic acid sodium salt To a suspension of Example 8 (309 mg) in isopropyl alcohol (30 ml), sodium hydroxide (107 mg) was added. The solution was heated at 60° C. for 4 hours, then the solvent was removed under reduced pressure. The residue was suspended in water, and the precipitate was filtered to give the title compound (250 mg) as a pale yellow solid.

¹H-NMR:(DMSO) 11.69(bs), 8.37(d), 7.75(bd), 7.39(d), 7.07(d), 6.98(d), 4.24(m), 2.12(m), 1.80–1.55(m), 1.40–1.10 (m), 0.99(m), 0.93(s), 0.84(s), 0.73(s)

IR(Nujol)cm$^{-1}$ 3431(NH), 3377(NH), 1647–1610(C=O)

EXAMPLE 17

(E) 3-[2'-(2"-adamantylaminocarbonyl) ethenyl]-4,6-dichloroindole-2-carboxylic acid sodium salt To a suspension of Example 9 (312 mg) in isopropyl alcohol (10 ml), sodium hydroxide (108 mg) was added. The solution was heated at 60° C. for 1.5 hours, then the solvent was removed under reduced pressure. The residue was suspended in water, and the precipitate was filtered to give the title compound (281 mg) as a white solid.

¹H-NMR:(DMSO) 11.8–11.6(bs), 8.34(d), 7.74(bd), 7.37 (d), 7.05(d), 6.88(d), 3.95(d), 2.03(d), 1.8–1.6(m), 1.46(d)

IR(Nujol)cm$^{-1}$ 1.1653(C=O), 1607(C=C)

EXAMPLE 18

Ethyl 3-(2'-(1-Adamantylcarbamoyl)-ethynyl)-4,6-dichloroindole-2-carboxylate

A solution of Intermediate 10 (303 mg) in THF (25 ml) and NaOH (5 ml, 2N) was stirred at room temperature for 2.6 h. HCl (30 ml, 1N) was then added to give a fine precipitate which was extracted with ethyl acetate (200 ml) and washed with brine to pH=6. The solvent was removed on the rotary evaporator to give a pink residue which was purified by column chromatography using 20% EA/CH followed by 5% EA/DCM to give the title compound (218 mg,)as a white solid.

IR (Nujol) $v_{max}$ (cm$^{-1}$) 3300 (NH), 2230 (triple bond), 1684 (C=O), and 1634 (C=C).

¹H-NMR (CDCl$_3$) 9.16 (s), 7.34 (d), 7.22 (d), 5.58 (s), 4.47 (q), 2.10 (m), 1.70–1.5 (m), and 1.49 (t).

EXAMPLE 19

3-(2'-(1-Adamantylcarbamoyl)-ethynyl)-4,6-dichloroindole-2-carboxylic acid sodium salt Sodium hydroxide (59 mg) was added to a solution of Example 18 (170 mg) in isopropyl alcohol (5.4 ml) and the reaction was heated at 60° C. for 3 h. After cooling, water (6 ml) was added and the resulting yellow precipitate was filtered and washed well with more water, then dried to furnish the title compound (157 mg,) as a white solid.

IR (Nujol) $v_{max}$ (cm$^{-1}$) 2230 (triple bond), and 1618 (C=C).

¹H-NMR (DMSO) 12.1 (br), 7.79 (s), 7.39 (s), 7.14 (s), 2.002 (m), and 1.6 (m).

EXAMPLE 20

(E) 3-[2-(1-adamantylcarbamoyl)ethenyl]4,6-dichloroindole-2-carboxylic acid

To a solution of Example 1 (180 mg) in ethanol (9 ml) and water (3 ml), lithium hydroxide monohydrate was added (49 mg). The solution was refluxed for 1.5 hours then the ethanol was evaporated under reduced pressure. Water (80 ml) was added to the residue and the solution was acidified with 1N HCl to pH=1. The white precipitate was filtered and washed with water to give the pure title compound (145 mg) tlc (DCM/EA/AcOH=60136/4) Rf=0.23.

IR(Nujol) Vmax (cm$^{-1}$) 3445–3144 (OH,NH), 1720 (C=O), 1659 (C=O), 1610 (C=C).

$^1$H-NMR(DMSO) 13.6(s), 12.4(s), 8.02(d), 7.58(s), 7.44 (d), 7.25(d), 6.55(d), 2.06–1.96(m), 1.64(m).

Pharmacy Examples

| A. Capsules/Tablets | |
|---|---|
| Active ingredient | 200.0 mg |
| Starch 1500 | 32.5 mg |
| Microcrystalline Cellulose | 60.0 mg |
| Croscarmellose Sodium | 6.0 mg |
| Magnesium Stearate | 1.5 mg |

The active ingredient is blended with the other excipients. The blend can be used to fill gelatine capsules or compressed to form tablets using appropriate punches. The tablets can be coated using conventional techniques and coatings.

| B. Tablet | |
|---|---|
| Active ingredient | 200.0 mg |
| Lactose | 100.0 mg |
| Microcrystalline Cellulose | 28.5 mg |
| Povidone | 25.0 mg |
| Croscarmellose Sodium | 6.0 mg |
| Magnesium Stearate | 1.5 mg |

The active ingredient is blended with lactose, microcrystalline cellulose and part of the croscarmellose sodium. The blend is granulated with povidone after dispersing in a suitable solvent (i.e. water). The granule, after drying and comminution is blended with the remaining excipients. The blend can be compressed using appropriate punches and the tablets coated using conventional techniques and coatings.

| C. Injection Formulation | |
|---|---|
| Active ingredient | 0.1–7.00 mg/ml |
| Sodium phosphate | 1.0–50.00 mg/ml |
| NaOH qs desidered pH (range 3–10) | 1 ml |
| water for injection qs to | |

The formulation may be packed in glass (ampoules) with a rubber stopper (vials, syringes) and a plastic/metal overseal (vials only).

| D. Dry Powder for constitution with a suitable vehicle | |
|---|---|
| Active ingredient: | 0.1–100.00 mg |
| Mannitol qs to | 0.02–5.00 mg | packed in glass vials or syringes, with a rubber stopper and (vials only) a plastic metal overseal.

| E. Inhalation Cartridges | |
|---|---|
| | mg/cartridge |
| Active ingredient (micronised) | 5.00 |
| Lactose to | 25.00 |

The active ingredient is micronised in a fluid energy mill to a fine particle size range prior to blending with normal tabletting grade lactose in a high energy mixer. The powder blend is filled into a proper unit dose Container as blister or capsule for use in a suitable inhalation or insufflation device.

The affinity of the compound of the invention for strychnine insensitvie glycine binding site was determined using the procedure of Kishimoto H. et al J. Neurochem 1981, 37, 1015–1024. The pKi values obtained with respresentative compounds of the invention are given in the following table.

| Example No. | pKi |
|---|---|
| 10a | 7.2 |
| 10b | 7.7 |
| 11 | 8.0 |
| 14 | 7.58 |
| 16 | 7.4 |
| 17 | 7.6 |

The ability of compounds of the invention to inhibit NMDA induced convulsions in the mouse was determined using the procedure of Chiamulera C et al. Psychopharmacology 1990, 102, 551–552. In this test the ability of the compound to inhibit the generalized seizures induced by an intracerebroventricular injection of NMDA in mice was examined at a number of dose levels. From these results the dose required to protect 50% of the animals from the convulsive action of the NMDA was calculated. This expressed as mg/kg is referred to as the $ED_{50}$ value.

Representative results obtained for compounds of the invention when given by intravenous and oral administration are given in the following table.

| Ex No. | $ED_{50}$ iv | mg/kg po |
|---|---|---|
| 10a | 0.02 | 5.47 |
| 10b | 0.01 | 11.1 |
| 14 | 0.05 | 6.0 |

The compounds of the invention are essentially non toxic at therapeutically useful doses.

We claim:

1. A compound of formula (I)

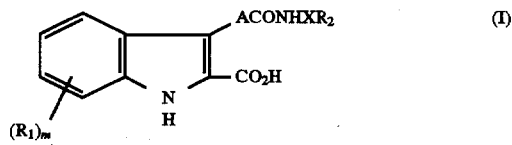

or a salt, or metabolically labile ester thereof wherein $R_1$ represents a group selected from halogen, alkyl, alkoxy, amino, alkylamino, dialkylamino, hydroxy, trifluoromethyl, trifluoromethoxy, nitro, cyano, $SO_2R_3$ or $COR_3$ wherein $R_3$ represents hydroxy, methoxy, or amino; m is zero or an integer 1 or 2;

A represents an ethynyl group or an optionally substituted ethenyl group;

X represents a bond or a $C_{1-4}$alkylene chain;

$R_2$ represents a bridged cycloalkyl or bridged heterocyclic group.

2. A compound as claimed in claim 1 wherein m is 2 and $R_1$ is chlorine at the 4 and 6 position.

3. A compound as claimed in claim 1 wherein X is a bond.

4. A compound as claimed in claim 1 wherein A is an ethenyl group in the trans configuration.

5. A compound as claimed in claim 1 wherein $R_2$ is a bridged cycloalklyl group containing from 7 to 10 carbon atoms.

6. A compound as claimed in claim 1 wherein $R_2$ is a group selected from 1-adamantyl, 3-noradamantyl or 2-exo-2-norbornanyl.

7. The compounds selected from the group consisting of:
(E)-3[2-(1-adamantylcarbamoyl)ethenyl]4,6-dichloroindole-2-carboxylic acid; and (E) 3-[2'-(noradamantyl-3"-aminocarbonyl) ethenyl]-4,6-dichloroindole-2-carboxylic acid and physiologically acceptable salts thereof or metabolically labile esters thereof.

8. A pharmaceutical composition comprising a compound as claimed in claim 1 in admixture with one or more physiologically acceptable carriers or excipients.

9. A method of treatment of man for conditions where antagonising the effects of excitatory amino acids with NMDA receptor complex is of a therapeutic benefit comprising administration of an effective amount of a compound as claimed in claim 1.

10. A process for preparing a compound as defined in claim 1 which comprises reacting an activated derivative of the carboxylic acid (II)

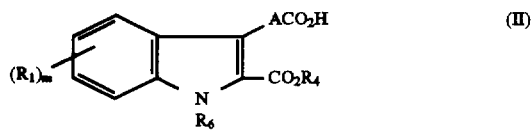

wherein:

$R_1$ is selected from the group consisting of halogen, alkyl, alkoxy, amino, alkylamino, dialkylamino, hydroxy, trifluoromethyl, trifluoromethoxy, nitro, cyano, $SO_2R_3$ and $COR_3$ wherein $R_3$ represents hydroxy, methoxy or amino;

m is zero or an integer 1 or 2;

$R_4$ is a carboxyl protecting group;

$R_6$ is hydrogen or a nitrogen protecting group; and

A is an optionally substituted ethenyl group, with an amine $NH_2XR_2$, wherein:

X represents a bond or a $C_{1-4}$alkylene chain; and $R_2$ represents a bridged cycloalkyl or bridged heterocyclic group, and thereafter if necessary or desired followed by one or more of the following operations:

(1) removal of the carboxyl protecting group $R_4$;

(2) removal of the nitrogen protecting group $R_6$;

(3) conversion of one compound of formula (I) or a protected derivative thereof into another compound of formula (I) or a protecting derivative thereof;

(4) conversion of the resultant compound of formula (I) or a carboxyl protected derivative thereof into a salt or metabolically labile ester thereof.

* * * * *